United States Patent [19]
Strandberg et al.

[11] Patent Number: 6,134,472
[45] Date of Patent: Oct. 17, 2000

[54] HEART STIMULATION DEVICE

[75] Inventors: Hans Strandberg, Sundbyberg; Johan Lidman, Stockholm; Kjell Norén, Solna, all of Sweden

[73] Assignee: Pacesetter AB, Järfälla, Sweden

[21] Appl. No.: 09/269,347

[22] PCT Filed: Sep. 22, 1997

[86] PCT No.: PCT/SE97/01590

§ 371 Date: Nov. 26, 1999

§ 102(e) Date: Nov. 26, 1999

[87] PCT Pub. No.: WO98/14240

PCT Pub. Date: Apr. 9, 1998

[30] Foreign Application Priority Data

Sep. 30, 1996 [SE] Sweden .................................. 9603574

[51] Int. Cl.[7] .................................................. A61N 1/365
[52] U.S. Cl. .......................................................... 607/24
[58] Field of Search .............................. 607/9, 18, 24, 607/23

[56] References Cited

U.S. PATENT DOCUMENTS 4,535,774  8/1985  Olson .
4,867,163  9/1989  Schaldach .
5,156,147  10/1992 Warren et al. .
5,417,715  5/1995  Noren et al. .
5,500,006  3/1996  Heinze .

FOREIGN PATENT DOCUMENTS 0 551 355  7/1993  European Pat. Off. .
0 634 192  1/1995  European Pat. Off. .

*Primary Examiner*—Scott M. Getzow
*Attorney, Agent, or Firm*—Hill & Simpson

[57] ABSTRACT

In the determination of an optimal rate for the delivery of stimulation pulses to a heart, the stroke volume (SV) of a heart ventricle is measured as a function of heart rate (HR), e.g. by determination of impedance in individual heart cycles whose duration is varied from the duration corresponding to the prevailing rate or the basic rate regarded as optimal for stimulation. The optimal rate should lie at the knee of this function. A corresponding knee is also found in the curve for cardiac output (CO). This rate is determined by calculation of an auxiliary function, e.g. HF=HR×CO, which displays a peak at the heart rate at which the knee is located, and the heart rate is determined which yields this maximum. The heart rate determined in this manner is subsequently employed as a basic rate.

10 Claims, 6 Drawing Sheets

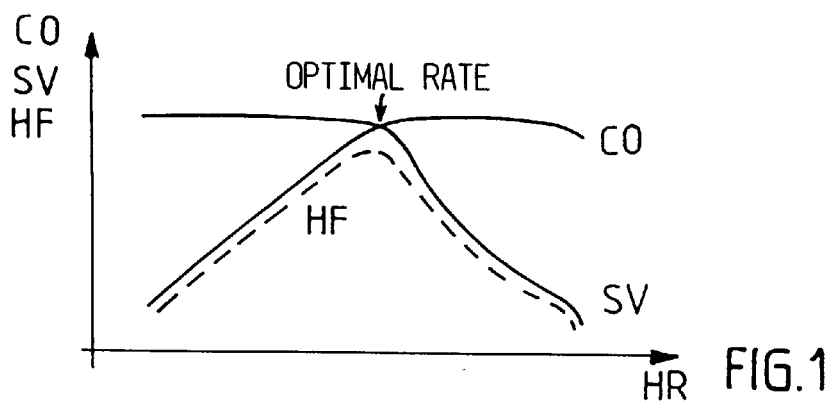
FIG. 1
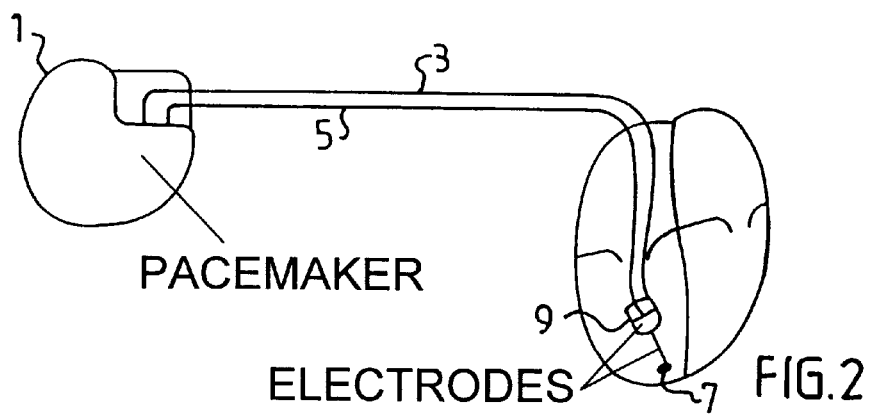
FIG. 2
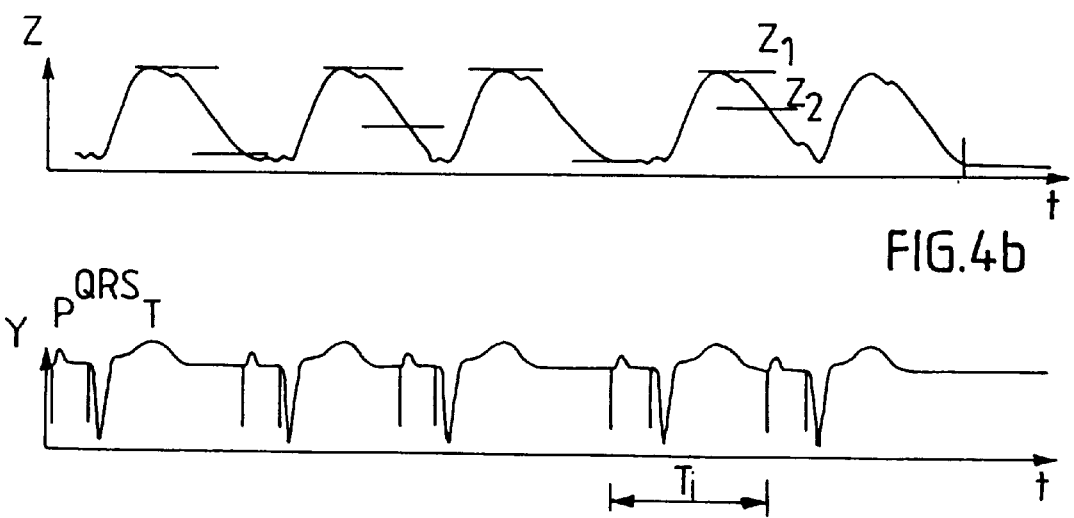
FIG. 4b
FIG. 4a

HEART STIMULATION DEVICE

BACKGROUND OF THE INVENTION

1. Field of the Invention

The present invention relates to devices for determining the optimal rate for emission of a stimulation pulse to a heart.

2. Description of the Prior Art

The ability to control the heart rate by means of electrical stimulation is important to the well-being and survival of many people afflicted by various defects in the function of their hearts. Battery-powered stimulation devices are available for different kinds of disorders.

The heart comprises a left atrium, right atrium, left ventricle and right ventricle and contains e.g. a sinus node (sinoatrial node. SA node), an area made up of special tissue in the wall of the heart's right atrium. In the normal, healthy state this area emits periodic, recurrent electrical pulses, each of which starting a heart cycle. When the pulse from the sinus node is propagated across the walls of the atrium, it triggers contraction of the atrium for expulsion of blood into the corresponding ventricle. The pulse is carried to another tissue area in the heart which has a special delay function, the atrioventricular (AV) node, from which it is carried on special electrically conductive tissue pathways to the ventricles. It is during this phase, when the electrical pulse passes along the conductive pathways to the ventricular walls, that blood is "pumped" from the atrium to ventricle. By the time this pulse arrives to trigger contraction of the ventricles, the ventricles have been expanded by inflowing blood and are ready to contract in order to pump blood to the lungs and circulatory system. After each contraction of the ventricles, a resting period starts during which the atria fill with blood, and lasts until the SA node generates the next pulse.

Normal rhythm, i.e. sinus rhythm, arises in the SA node. A faulty rhythm or rate, i.e. arrhythmia, can develop for different reasons. For example, the pathways, made of electrically conductive tissue, to or in a ventricle may be damaged or blocked so pulses emitted in the atrium are unable to trigger any contraction of the ventricle. In such cases, an electrical stimulation pulse can be supplied by an electronic stimulation device, i.e. a pacemaker. The generating of stimulation pulses by most of the stimulation devices currently in use is synchronized with or generally dependent on the heart's intrinsic electrical activity. This activity can be monitored with sensor electrodes placed somewhere in the patient's body, e.g. in or adjacent to the heart.

These sensor electrodes in an appropriate system sense electrical voltages generated during heart activity. The electrical voltage sensed with surface electrodes on the exterior of the body has the following general morphology during a heart cycle: A low voltage pulse, the P wave, designates an atrial event, corresponding to depolarization of muscle cells in the walls of the atria, causing these walls to contract. A more complex pulse segment is referred to as the QRS complex and encompasses e.g. a large electrical pulse. This area designates a ventricular event in the form of depolarization of muscle cells in ventricular walls when these cells contract, and the heart's actual blood-pumping process is started and performed. A low voltage pulse further designates the start of repolarization of the cells in ventricular walls, i.e. recovery from their preceding contraction, and is referred to as the T wave. These pulses/pulse segments normally follow each other over time, i.e. a P wave starts first in a heart cycle, followed by the QRS complex and, finally, the T wave. These segments are not always distinguishable in the electrical voltage sensed by sensor electrodes placed in or by the heart. Thus, no T wave and often not even the QRS complex are discernible with an electrode placed in an atrium. The P wave is not visible with an electrode in the ventricle.

A typical stimulation device can operate in the following general manner: The stimulation device awaits an atrial event, signaled by corresponding electrical activity in the heart, i.e. in practice the aforesaid P wave. If no P wave is detected within a first period of time (an atrial escape period), a stimulation pulse is sent to the atrium of the heart, stimulating muscle cells in atrial walls and causing them to contract. A ventricular event is then awaited, i.e. the device analyzes the voltage signal from the heart with respect to the presence of a QRS complex. If no such complex is detected within a second period of time (a ventricular escape interval), a stimulation pulse is sent to the ventricle, whereupon electrical activity in the atrium is again awaited. The interval between emission of stimulation pulses to the atrium and ventricle is equal to the difference in time between the first and second interval and is referred to as the AV delay. It normally corresponds to an interval lasting 100–200 milliseconds.

Normally, rate-modulating stimulation devices in current use determine the rate for emitting stimulation pulses as a function of the measurement value(s) for one or a plurality of parameters related to the physical load to which a person is subjected. These measurement values are sensed by suitable sensors devised in different ways. One such sensor can be an electrically powered flow meter, as shown in the published European patent application 0 634 192. In other instances, the impedance of a heart ventricle is determined and, accordingly, stroke volume. Electrical impedance is measured between a stimulation electrode in a ventricle and some other electrode in the body or, especially. the heart, as is the case in U.S. Pat. No. 5,417,715 which is included as a reference.

In certain embodiments, e.g. as described in the aforementioned U.S. patent, only the ongoing heart cycle is reviewed, and an appropriate time for the generating of a stimulation pulse is mainly determined from measurement values previously obtained in the same cycle, whereas measurements in previously proposed embodiments are made over a plurality of heart cycles which, in certain instances, may be well-separated in time. In principle, as is also discussed in the aforementioned U.S. patent, a well-selected or advantageous time for stimulating a heart is deemed to be when there is sufficient blood in a ventricle for it to be pumped out of same. Such a stimulation largely resembles the one which occurs naturally in a healthy heart. So an effort should be made to select a heart rate enabling these times to be achieved or at least times which are not too far removed from them. Heart stimulator designs supplying such times are previously known through e.g. the aforementioned U.S. patent and are discussed below.

The European patent EP-B1 0 551 355 shows how the interval elapsing between two consecutive stimulation pulses is continuously varied or reset with the aid of measurement of a parameter for the heart's activity. The parameter is measured as related to a single change in the duration of the stimulated heart cycle compared to the measurement value for the preceding heart cycle. The individual changes, only made for measurement purposes, are performed with intervals between them which do not affect general pressure in the circulatory system. The parameter is impedance between e.g. an electrode placed in the heart and a pacemaker housing, and this impedance represents, or is related to, the heart s stroke volume. The ratio is formed between impedance changes, with changes of equal but opposite magnitude, in the interval between stimulation pulses, and this value is compared to a reference value which can be constant or dependent on heart rate. When hemodynamic rate optimization is proposed, the time elapsing between two stimulation pulses is reduced on individual occasions until the change in impedance stops increasing. a procedure supplying a measure of the stroke volume. Here, it must be assumed that normal stimulation is too slow and utilizes a sub-optimal stimulation rate, which should be the result with a rate corresponding to the interval used when the change in impedance stops increasing.

U.S. Pat. No. 5,156,147 shows an adaptive pacemaker in which the change in the heart's pumped volume per unit of time, i.e. cardiac output (CO). is determined when heart rate increases. If the change is negative, i.e. reduced cardiac output then results, the increase in heart rate is canceled. It also notes that the increase in one possible embodiment can be also canceled if the increase in heart rate causes a drop in the increase rate for cardiac output.

SUMMARY OF THE INVENTION

An object of the invention is to provide a device which simply and effectively controls the emission of stimulation pulses at a rate or with a rhythm selected so the function of a heart receiving these pulses simulates, to a great degree, the function of a normally working heart, thereby preventing the imposition of needlessly heavy strain on heart muscle at any given load.

Another object of the invention is to provide a device for delivering stimulation pulses to a person s heart at a rate or rhythm which is automatically adjusted to the work load sustained by the person.

Thus, the problem the present invention will solve is to provide a stimulation devices which determines, in a safe and effective fashion, optimal times for the generating of stimulation pulses through the use of reliable and, preferably, simple algorithms. The times for pulse emission must also be constantly adapted to a person's prevailing physical work load.

It is assumed, in the same way as in the aforesaid U.S. Pat. No. 5,417,715, that the time at which a stimulation pulse is to be generated is selected in such a way that optimal filling of a heart ventricle is achieved in each cardiac cycle. Thus, the slowest possible heart rate is thereby used for each load situation, i.e. the amount of blood required per unit of time to accommodate the physical work load, thereby imposing light strain on heart muscle. In determinations of this time and the corresponding heart rate and stimulation interval, in which the stimulation interval is the time elapsing between consecutive stimulation pulses, the stimulation interval is varied around the value selected for the moment in a wav similar to the procedure described in the aforesaid patents European Patents 0 551 355 and U.S. Pat. No. 5,156,147, and a measure of the degree of filling is determined as a function of heart rate.

Heart cycle durations corresponding to a plurality of different heart rates are used, then supplying measurement values for the corresponding degree of filling.

In order to achieve simple and reliable determination of the optimal interval, an appropriate mathematical function of both heart rate and a degree of filling is selected which achieves an extreme point, e.g. a peak value, at the optimal heart rate. Such a design could also simplify and improve the efficiency of control and calculation circuits in the stimulation device. A heart rate is selected which supplies the function an extreme value, a peak value in particular, and it is subsequently used as a new optimal heart rate. One preferred mathematical function is the arithmetic product of heart rate and stroke volume raised to the second power.

According to the aforesaid U.S. Pat. No. 5,156,147, a mathematical function, cardiac output, which is the arithmetic product of heart rate and stroke volume, is used in determining the optimal heart rate. In this function the heart rate is determined at which the function displays a knee, i.e. changes from an essentially constant progression to a declining progression. A knee obtained at the intersection of two straight lines or curves is easily defined, of course, since it is found at the intersection between the lines and curves respectively. For functions obtained or measured in physical processes and which develop a knee in some area, the knee generally consists of a gentle transition between e.g. two mainly straight lines. It is then mathematically difficult to define, unequivocally, the point in the gentle transition at which the knee is located or should be located. One such determination of the location of a knee in a function in a physically determined function will then be much more difficult and unreliable than determination of e.g. a peak value for a physical function. Determination of a knee also requires more complex algorithms, which can contain different logical choices or comparisons and are, therefore, non-standard, which must be processed by the electronic calculation circuits in the stimulation device, increasing, in turn, circuit complexity. Increased circuit complexity can, in turn. increase the circuits' power consumption.

The electrical impedance measured between an electrode placed in a heart ventricle and another electrode, which can be placed inside or outside the heart, is related to the amount of blood in a heart ventricle. In particular, impedance can be determined when it reaches a peak value, which occurs when the heart ventricle contains a minimum amount of blood. Impedance can further be determined in the same heart cycle immediately before blood is ejected out of the ventricle when the nadir value for impedance is achieved, i.e. in practice immediately before the emission of a stimulation pulse, e.g. a pulse for stimulating an atrial contraction. The difference between impedance values measured in the same heart cycle constitutes a relative measure of stroke volume, so this difference, within certain limits, can be regarded as a strictly declining function of stroke volume, thereby resulting in a one-to-one ratio between the value for impedance and the value for stroke volume. Instead of a function of heart rate and stroke volume, a corresponding function of heart rate and the impedance difference can be used which has extreme values for the same values for heart rate. Thus, a function can be used which is the product of heart rate and the impedance difference raised to the second power.

When an appropriate sign is selected, the chosen function can always be made to have a peak at a given heart rate, henceforth referred to as "the optimal heart rate". The heart rate supplying this peak value can be determined in different ways.

One simple method is to have the pacemaker stimulate at a fixed rate and assign occasional intervals a length which deviates from the length of intervals in the fixed rate. Some kind of determination of stroke volume is performed, at least for the heart cycle with an altered duration, e.g. impedance is measured, and the value of the selected function can be calculated. This value for the function is compared to a corresponding value for a function calculated in the immediately preceding determination. If the new functional value proves to be larger, the interval used for determining that value is closer the heart cycle duration corresponding to the optimal heart rate. The interval with the altered duration is then used thereafter, and the fixed heart rate is changed to correspond to a heart cycle employing the interval's length. Otherwise, the interval used in the fixed heart rate temporarily set is closer to the heart cycle duration employing the optimal rhythm. No change in the fixed heart rate set then needs to be made.

However, it is not known in either instance whether the selected heart rate is optimal, so an individual interval is again assigned a differing duration. The duration of this interval can be selected e.g. so the change in relation to the prevailing fixed heart is in the opposite direction to the change resulting in a lower functional value in the preceding determination using a test interval with a deviating duration. In a somewhat different procedure, the difference between the duration of the new interval set and the duration of the interval corresponding to the prevailing fixed rate is assigned an arithmetic sign opposite to the sign for the immediately preceding test interval in instances in which no change was made in heart rate. In instances in which a change is made, the sign for the difference can be set at the same sign as for the difference calculated for the preceding test interval. These changes in the duration of individual heart cycles are made until two consecutive functional values have been calculated which fail to produce any change in the prevailing fixed rate. The prevailing fixed rate is then as close to the optimal value as can be determined with this stepping method.

In instances in which functional values for two consecutive test intervals are identical, it can be assumed that the optimal rate corresponds to a heart cycle duration between the durations of these test intervals. The optimal rate can then be set at a value corresponding to e.g. one heart cycle duration which is the mean value of the duration of these test intervals.

If other anomalies are present in measurement values, such as the formation of plateaus in the morphology of the selected function, this simple procedure could lead to unreliable optimization of the heart rate. In order to reduce errors caused by measurement data. measurement values, determined for more than two intervals with different durations and weighting of the functional values calculated from these measurement values, are preferably used for determining an optimal heart rate. Thus, a measurement procedure can be used entailing variation in heart cycles, chronologically separated from each other, in which the prevailing heart rate generally employed is varied in the same wav as in the aforesaid European patent 0 551 355. The values for the selected functions are calculated for the various heart cycles set, especially for heart cycles with deviating lengths, and the heart cycle duration producing peak functional performance is determined from these functional values. The simplest way to perform a determination is to take the heart cycle duration, and associated heart rate supplying the peak value, and using this rate as the new heart rate. A more accurate and reliable determination can be made by approximating the calculated values with a simple function, e.g. a second degree function such as a parabola, and calculating the corresponding heart cycle duration from the peak value of the approximated function which is thereupon utilized in stimulating the heart.

However, this procedure can be needlessly complex and result in excessively long regulation times. Since rapid adaptation of heart rate to new and changed physiological requirements is sometimes necessary, a more appropriate procedure might be to conduct continuous searches so the duration of each stimulation interval differs from the duration of the preceding interval. Changes from the optimal heart cycle duration should then differ so little that there is no perceptible change in average blood pumping capacity while still being as large as possible to enhance accuracy in determination of stroke volume and, in particular, in determination of differences in impedance. A new optimal heart rate is calculated for each heart beat from the most recently calculated functional values. Alternately, a new optimal heart rate can be calculated after every series of a number of consecutive heart cycles with varying durations, the number being greater than two, e.g. four, calculations only being based on functional values determined for the heart cycles in this series. In one preferred embodiment, therefore, impedance measurements can be made for a plurality of consecutive heart cycles whose duration is varied from a heart cycle duration assumed to be the best at the moment and corresponding to the optimal heart rate as above. The heart cycle duration therefore is changed for each new cycle, and this should be performed so the average interval between stimulation pulses is essentially the same as the calculated optimal duration at the moment or equal to a reference value for duration, at least for the intervals between several consecutive stimulation pulses. The duration of intervals between stimulation pulses should also deviate in an alternating fashion from the reference value so the duration of every other interval exceeds the reference value, and the duration of every other interval is less than the reference value.

In these methods with continuous searches the optimal heart rate, corresponding to the reference value for stimulation intervals, is constantly adjusted. Stimulation is not performed exactly so the reference value is obtained for the next heart cycle and stimulation interval but with an appropriately selected deviation so a possible new reference value can speedily and reliably be found. An additional improvement in the determination of the optimal heart rate can be achieved when calculations allow a new reference value to relate to the immediately preceding reference values, e.g. so no changes are made which are too fast and/or too large, with the aid of recursive low pass filtration of the reference values.

In the embodiments discussed above, only a few current values are compared, and no absolute reference is needed for the measured signal. The impedance measurement therefore only needs to be stable for a relatively brief period of time. However, Impedance measurement must display good sensitivity.

DESCRIPTION OF THE DRAWINGS

FIG. 1 is a graph showing a curve of a physiological variable, and two derived curves as a function of heart rate, for use in accordance with the present invention.

FIG. 2 schematically illustrates a pacemaker connected to a heart for ventricular stimulation.

FIG. 4a is a typical electric cardiogram.

FIG. 4b is a graph showing how impedance measured across a heart variable, varies as a function of time, with the same scale as the electric cardiogram of FIG. 4a, this variation being used in accordance with the principles of the present invention.

DESCRIPTION OF THE PREFERRED EMBODIMENTS

Figure 3:
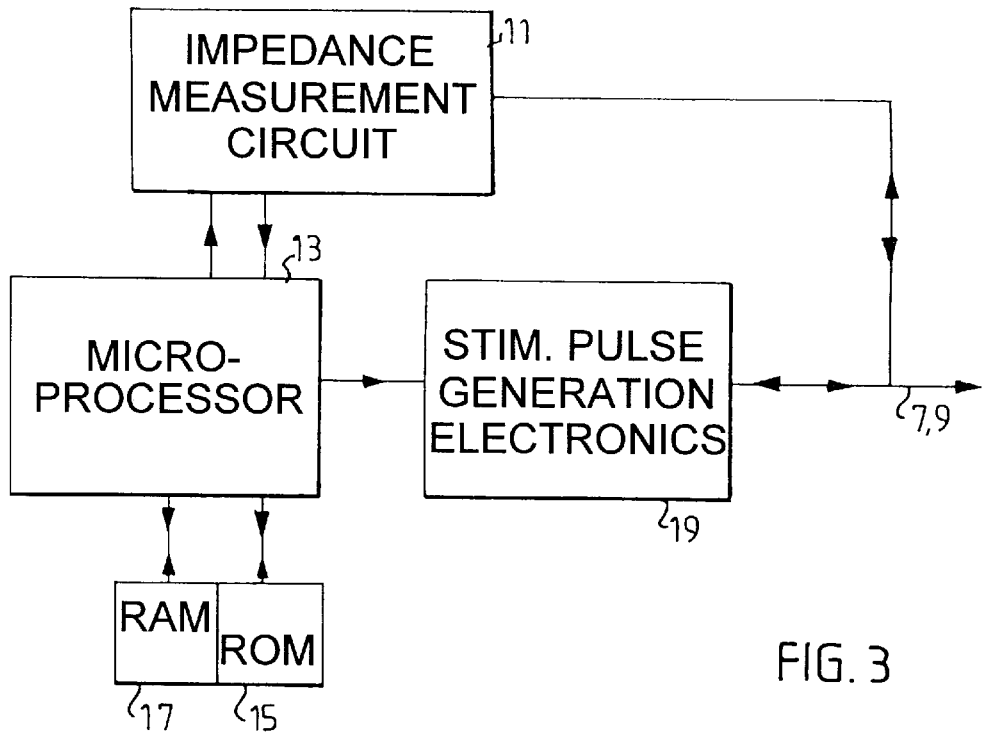
FIG. 3 is a block diagram of a stimulation device constructed and operating in accordance with the principles of the present invention.

FIG. 1 shows different units characteristic of a heart's pumping of blood as a function of the heart's rhythm or rate. The solid line SV designates the heart's stroke volume, i.e. the amount of blood pumped by a heart ventricle in one heart cycle. When the heart rate is slow, stroke volume is directly related to the heart ventricle's maximum blood-filled volume before the ventricle contracts to eject blood. As FIG. 1 shows, stroke volume in the depicted area displays relatively constant progression as heart rate increases, but the curve starts a uniform, linear descent from a breakpoint. The descending curve indicates that the heart ventricle did not have enough time to fill completely with blood at fast rates. The curve CO designates the volume of blood ejected per unit of time, i.e. cardiac output, and is the product of stroke volume SV times heart rate HR. The curve CO displays corresponding progression with a breakpoint at the same value for heart rate. So this curve is generally linear up to the breakpoint, thereafter displaying an essentially constant morphology. The optimal rate at which the heart should preferably be stimulated in order to achieve the slowest possible heart rate, commensurate with accommodation of the external physical work load and supplying the lungs or circulatory system with the requisite flow of blood, lies somewhere near the breakpoint.

The location of the breakpoint can be adaptively determined, as shown in U.S. Pat. No. 5,156,147. by increasing and reducing heart rate in steps and determining whether cardiac 5 output increases or remains constant. However, indicating a criterion for e.g. the condition that the curve CO must be essentially constant is difficult. Another overlooked difficulty is to clearly define a breakpoint on a curve in the area in which there is a smooth transition between two curve segments with differing morphologies. So it would be desirable if an extreme point, such as a peak for a suitable function, could be sought instead. In principle, a peak can generally be determined in simple comparisons and is much easier to determine than the said breakpoint between a linear, rising or falling segment and a segment with constant progression. Various possible, new functions can be derived from the general progression of the functions shown in FIG. 1. Thus, suitable linear functions can be subtracted from the curves SV and CO. Another possibility is to form some suitable product from factors containing HR and SV in which these could be e.g. powers. One such curve HF is shown with the dashed line in FIG. 1 and was derived from the relationship $HF = HR \cdot SV^2 = SV \cdot CO$, i.e. it is a product of the curves shown with solid lines in FIG. 1.

Determination of maxima according to the above can be performed in a heart stimulator 1 (see FIG. 2 in which its connections to a heart are schematically depicted.). The stimulator or pacemaker 1 is connected by electrical leads 3 and 5 to an end electrode 7 and a ring electrode 9 connected to a heart. The stimulator 1 emits and delivers stimulation pulses to the heart across the electrodes 7, 9.

The internal structure of the stimulation device 1 is shown in the overview block diagram in FIG. 3. An impedance measurement circuit 11, connected to the electrode leads 3 and 5, is used for determining the amount of blood in the heart ventricle and, accordingly, stroke volume. At intervals determined by a microprocessor 13, it emits an e.g. 4 kHz alternating current low-amperage signal with a brief duration. During this time, electrical impedance, i.e. electrical current in relation to the applied voltage signal, is measured. The microprocessor 13 receives the measured impedance value from the impedance measurement circuit for additional processing. Alternately, impedance can be measured between an electrode in the heart ventricle and an electrode located outside the heart, such as the metal enclosure which conventionally houses the stimulation device.

The microprocessor 13 is further connected to a read-only memory 15, ROM. and a read/write memory 17, RAM. It sends information to electronic circuits 19, for emitting stimulation pulses, containing various control circuits for e.g. detecting electrical events in the heart which designate atrial or ventricular contractions.

With the described construction, the microprocessor 13 is able to measure electrical impedance at appropriate times in order to obtain a measure of the of ventricular filling. Measuring impedance $Z_1$ (see FIG. 4a discussed below) can be appropriate at the time at which impedance reaches a peak value, and the heart ventricle has been emptied. This occurs at an approximately fixed time about 250 to 300 milliseconds after the stimulation pulse (cf. FIG. 4b and the discussion below). The impedance $Z_2$ can be further measured immediately prior to emission of a stimulation pulse. The difference $\Delta Z = Z_1 - Z_2$ between measurement values provides a measure of stroke volume. A function $HF_Z$ suitable for maximization can be calculated from $HF_Z = (Z_1 - Z_{Z2})HR$. And according to the above, it is approximately proportional to HF and has the same extreme values. An additional impedance measurement could also be made, in which case it is made between the described measurements at a fixed interval after the stimulation point, the interval being considerably longer than the first. A more complicated expression for a suitable function is then obtained for use in optimization.

Figure 7:
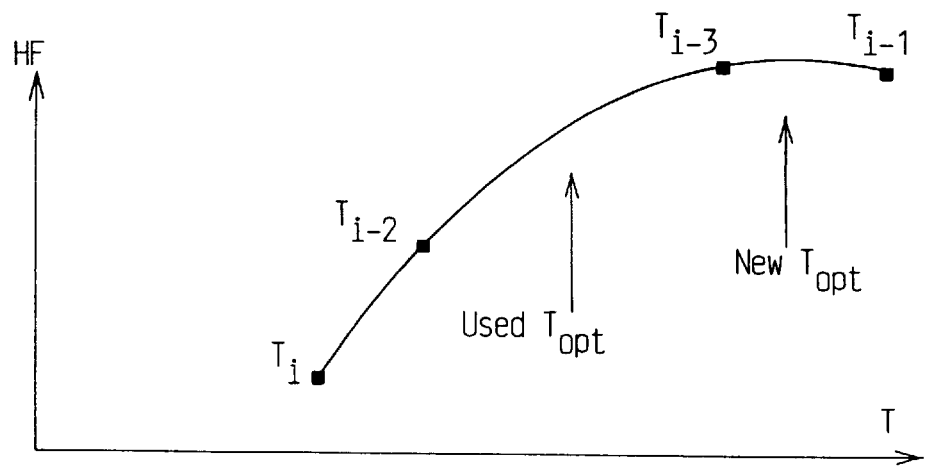
FIG. 7 is a graph showing the auxiliary function HF calculated in accordance with the invention, relative to the stimulation interval T.

In subsequent determination of the heart rate or corresponding stimulation interval supplying the aforesaid peak value, the time elapsing between two stimulation pulses is varied for a plurality of consecutive heart cycles, i.e. cycle duration is varied. The impedance difference according to the above is determined for these cycles so the differences form a function of the stimulation interval or, equivalently, heart rate. As shown in the diagram in FIG. 7, the function can be determined for e.g. four different stimulation intervals, designated $T_{i-3}$, $T_{i-2}$, $T_{i-1}$, $T_i$. The impedance difference for the stimulation interval $T_{opt}$ deemed to be optimal for the moment can obviously also be easily calculated and used, even if this is unnecessary. The changed stimulation intervals can e.g. be selected to lie symmetrically in pairs around the optimal stimulation interval, such as $T_{i-3} = T_{opt} + \Delta T$, $T_{i-2} = T_{opt} - \Delta T$, $T = T_{i-1} = T_{opt} + 2 \cdot \Delta T$, $T_1 = T_{opt} - 2 \cdot \Delta T$, in which $\Delta T$ is a suitably small increase in the stimulation interval. As a rule, such variations in cycle durations do not cause the patient much discomfort or disrupt cardiac function, provided variation values are small. A maximum variation in cycle duration, corresponding to a rate change of ±5 heart beats a minute, is therefore permissible in many cases. $\delta T$ in the example above would then correspond to a rate change of 2.5 beats a minute. Another paired, symmetrical distribution of measurement points around $T_{opt}$ yielding a uniform distribution is provided by $T_{i-3} = T_{opt} + \Delta T$, $T_{i-2} = T_{opt} - \Delta T$, $T_{i-1} = T_{opt} + 3 \cdot \Delta T$, $T_1 = T_{opt} -$ 3·ΔT. In this instance. δT corresponds to a rate change of 5/3=1.67 heart beats/minute. The deviations in these examples are such that positive and negative deviations occur alternately, and deviation with a positive sign is followed by deviation of the same magnitude but with a minus sign, whereby each pair of deviations acquires a mean value equal to the optimal stimulation interval. The mean value of the deviations following a change in the optimal stimulation interval will also be equal to the optimal stimulation interval until the next change in the optimal stimulation interval.

An alternative to this procedure is to measure only the difference in impedance at a single change in the duration of the stimulation interval and then to use only e.g. the four or five latest difference values in determining the function's maximum HF so more "continuous" determinations are made. However, this can require a rather complex choices for the duration of the changed stimulation interval.

Alternately, e.g. in cases in which such successive changes in the duration of the heart cycle would be too uncomfortable to the patient, the procedure according to the aforesaid European patent 0 551 335 can be used. In this procedure, the interval between two stimulation pulses during individual, non-consecutive heart cycles, separated by a plurality of heart cycles with a regular stimulation interval deemed to be optimal at the time, can be varied.

The value of the function HF according to the above can be calculated from the impedance differences and associated values for the duration of stimulation intervals. According to one simple procedure, a new, optimal stimulation interval $T_{opt}$ yielding the largest value for the function HF can be selected from the values for which impedance measurements were made.

Alternately, a curve fitting method can be used for determining a point at which HF has a maximum value. A suitable function is selected which displays a reasonable simple progression, whose fitting to measured HF values can be expected (cf. FIG. 1). i.e. the peak of the dashed curve. One such function which can be easily calculated and used is a second degree function, i.e. a parabola. $HF_{z,par}=A \cdot (T-T_{opt,new})_2+B$, in which A, B. $T_{opt,new}$ are constants determined during fitting, and $T_{opt,new}$ directly designates the stimulation interval value for which this function has a maximum. The second degree function can also be written $HF_{z,par}=a+bT_0+cT_0^2$ in which a, b, c are constants. See the discussion of FIG. 6 below. If only three measurement values are used in determining the maximum, the constants can be calculated by solving a linear equation system with three unknowns. If a number of measurement values are to be taken into account in the determination, the constants are determined with the aid of some kind of regression analysis. For example, recursive adjustment of the constants can be made until the absolute error between the measurement values and the function falls below a predefined value.

Figure 5A:
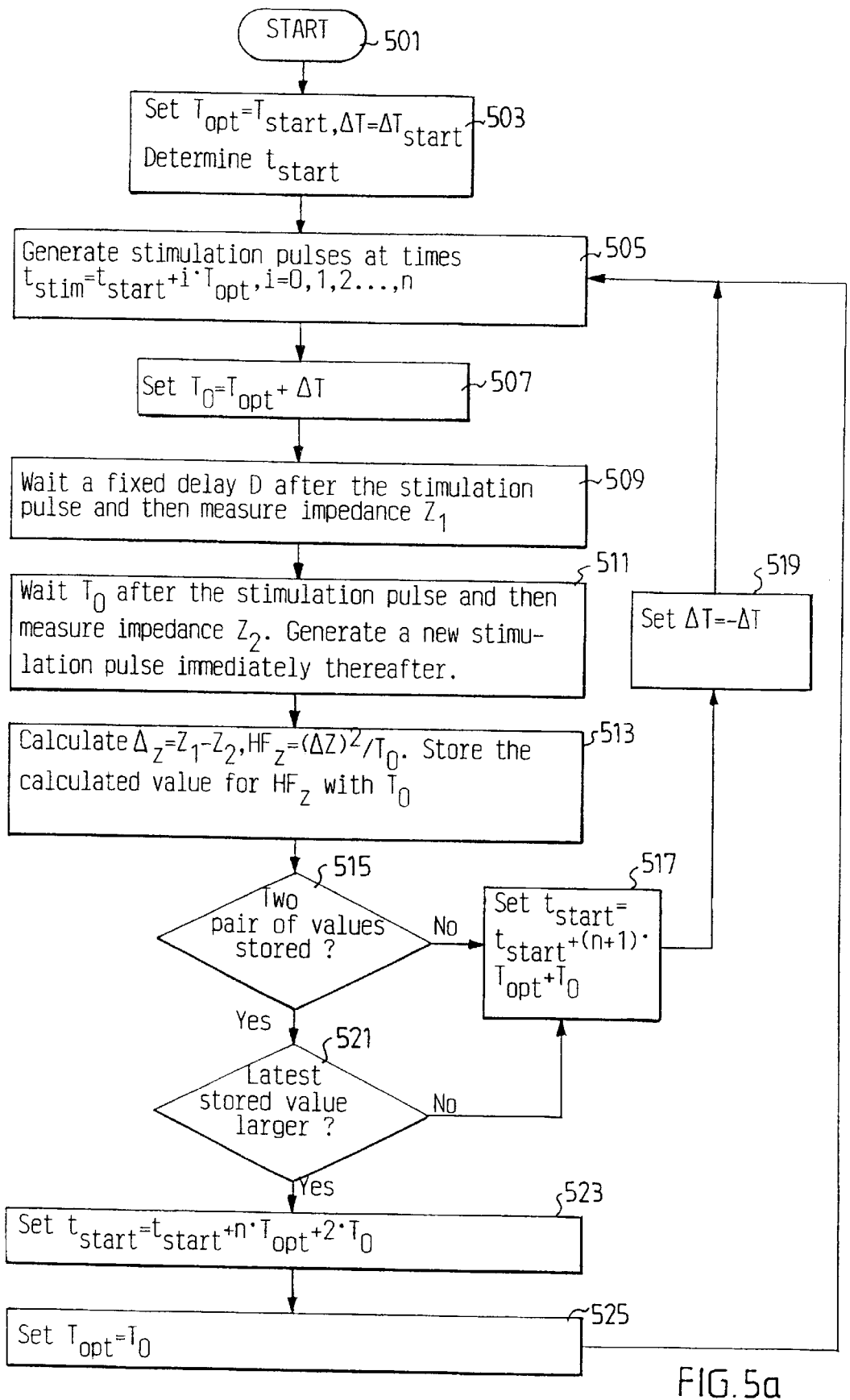
FIGS. 5a–5c are flowcharts showing steps performed in a micro-processor within a heart cycle employing different inventive algorithms.

The aforementioned determination methods are discussed in detail below in conjunction with comments on FIGS. 4a and 4b and the flow charts in FIGS. 5a–5c. FIG. 4a shows a diagram of electrical voltage at points on the body, located on opposite sides of the heart, for a heart stimulated by a pacemaker. One such voltage curve is called a surface electrocardiogram, and its general morphology was discussed above. The P and T waves appear as small positive pulses, whereas the QRS complex is characterized by a large negative pulse. The stimulation pulses are visible in the FIG. as negative, i.e. downward pointing, spikes for both atrial and ventricular stimulation, a spike appearing immediately before the P wave and immediately before the QRS complex. This means that the device according to FIG. 2 must be augmented with an atrial electrode, an associated electrical lead and control and drive circuits. Cf. U.S. Pat. No. 5,417,715 (FIG. 6) cited above. However, the stimulation pulses referred to below are only ventricular stimulation pulses. The pacemaker 1 is unable to generate a surface electrocardiogram according to FIG. 4a but can only pick up electrical voltage between points inside the body, said voltage displaying a somewhat different chronological progression. Cf, the discussion above. For example, the voltage between the end electrode 7 and the metallic surface of an enclosure housing the stimulation device 1 can be picked up and used by the stimulation device for detecting atrial and ventricular events in the known fashion. Alternately, voltage can be determined between the end electrode 7 and the ring electrode 9.

The diagram in FIG. 4b shows electrical impedance, measured e.g. between the end electrode 7 and the ring electrode 9, as a function of time for the heart for which the electrocardiogram in FIG. 4A was recorded. According to the above, the impedance is a function of the degree of heart ventricle filling and has an area comprising its largest values immediately before and/or around the T wave when the heart ventricle can be assumed to be as empty of blood as possible. The lowest values are found in the area immediately before and/or at the start of the QRS complex, corresponding to maximal filling of the heart ventricle.

The sequence of different steps performed by the microprocessor 13 will now be described, referring to the flowchart in FIG. 5a, for a first conceivable embodiment, entailing a simple search for a maximum. The method starts from starting block 501, and $T_{opt}$ is subsequently initiated in a block 503 at an appropriately selected value $T_{start}$. Moreover, a variable $\Delta T$ is assigned a starting value $\Delta T_{start}$. This variable $\Delta T$ can have both a positive and negative value and designates the time shift in the interval $T_{opt}$ used for stimulation to be used for the next impedance measurement when the interval $T_{opt}$ is changed for a single heart cycle to $T_{opt}+\Delta T$. A suitable time tSt,, is further determined at which the first stimulation pulse is to be Generated. In the next block 505. stimulation pulses are Generated at the times $t_{stim}=t_{start}+i \cdot T_{opt}$ in which i runs through the integers 0, 1, 2 . . . , n, n being a suitably selected whole number, $n \geq 0$ in which n can advantageously have a value greater than 1.

When these stimulation pulses have been Generated, an impedance measurement is performed in the next heart cycle, and the next heart cycle's interval is set in block 507 at $T_0=T_{opt}+\Delta T$. Impedance $Z_1$ is measured in block 509 after a given fixed delay D, on the order of 250–300 ms. after the last stimulation pulse. The delay D is selected so the heart ventricle in this impedance measurement is as empty of blood as possible. i.e. measurement is made when the value for impedance is about maximal. See FIG. 4b. The time at which measurement is made is then $t_1=t_{start}+n \cdot T_{opt}+D$. An additional impedance measurement is then made in the next block 51 1 with the measured impedance $Z_2$ in the same heart cycle, immediately before (i.e., by a small positive time δT) the next stimulation pulse and, thus, at the time $t_2=t_{start}+n \cdot T_{opt}+T_0-\delta T=t_{start}+(n+1) \cdot T_{opt}+\Delta T-\delta T$. The stimulation pulse is then emitted at the time $t_{stim}=t_{start}+(n+1) \cdot T_{opt}+\Delta T$. In the block 513, a value for the function $HF_z$ is calculated from the relationship $HF_z=(Z_1-Z_2)^2/T_0=\Delta Z^2/T_0$. The inverted value of the duration $T_0$ of an heart cycle interval corresponds to the heart rhythm. The value for $HF_Z$ is stored, with the current $T_0$ value, in RAM memory 17. See FIG. 3.

A determination is then made in block 515 as to whether two such values for HF, are stored for different $T_0$ values. If this is not the case, the block 517 is executed, whereupon the starting value $t_{start}$ for the next stimulation pulses emitted is set at $t_{start}=t_{start}+(n+1)\cdot T_{opt}+T_0$. The arithmetic sign for the time delay value $\Delta T$, i.e. a positive interval shift, is set at a negative value of the same absolute magnitude and vice-versa, is then changed in a block 19, and block 505 is repeated. If block 515 found that two $HF_z$ values were stored, block 521 is performed instead. These stored values are compared to each other in this block, and if the most recently stored value is smaller than the immediately preceding stored value, there is no need for any change in the optimal rate, and block 517 is again executed as above. Otherwise, i.e. if the latest functional value determined was larger, a change will be made, and the new starting value $T_{start}$ is first set in block 523 to $t_{start}+n\cdot T_{opt}+2\cdot T_0$. Cf block 517 above. The change is made when the optimal interval $T_{opt}$ is set at $T_0$ in block 525. Since the change in the duration of the heart cycle in this instance proved to yield a higher functional value, the same deviation value $\Delta T$ can be used as before in the search for an optimal heart cycle duration. After block 525, the cycle is therefore repeated, beginning with block 505.

Figure 5B:
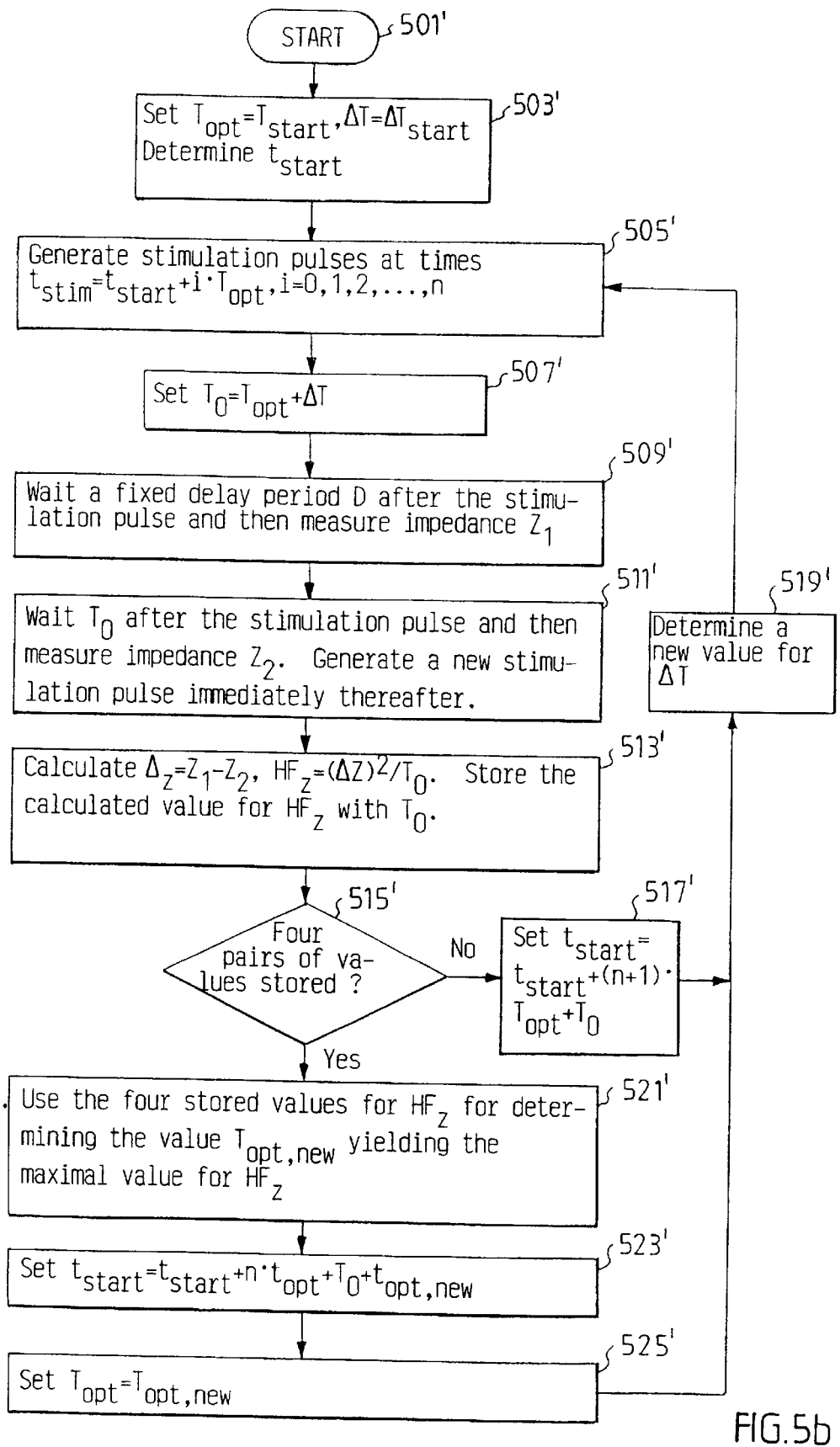

A search for an optimal heart rate by determination of a maximum based on a plurality of values and using the general procedure described in the European patent EP-B1 0 551 355 cited above is shown in the flowchart in FIG. 5b. In principle, the procedure utilizes the same first steps 501'–513' as in the steps 501–513 described for FIG. 5a above. However, values for the parameters can differ, so $\Delta T$ can differ, and n is always $\geq 1$. But the block 515' is different, and determinations are made in it as to whether four values for $HF_z$ are stored for different $T_0$ values. If this is not the case, block 517', which is the same as block 517 in FIG. 5a, is executed. A new value for the time delay $\Delta T$ is then selected in block 519' in some suitable manner, e.g. as discussed above and block 505' is executed once again. If block 515' found four $HF_z$ values stored, block 521' is executed. This block utilizes the stored functional values for determining the value $T_{opt,new}$ for the heart cycle duration yielding a maximum value for $HF_z$. A simple algorithm for this will be described below in conjunction with comments on FIG. 6. The determined value $T_{opt,new}$ will henceforth be used. To this end, the new starting value $t_{start}$ is first set at $t_{start}+(n+1)\cdot T_{opt}+T_0+T_{opt,new}$ in block 523'. Finally, the interval duration $T_{opt}$ is set at $T_{opt,new}$ in block 515. Block 519' is then executed as above with a new value for time deviation $\Delta T$, whereupon the entire process is repeated starting at block 505.

Figure 5C:
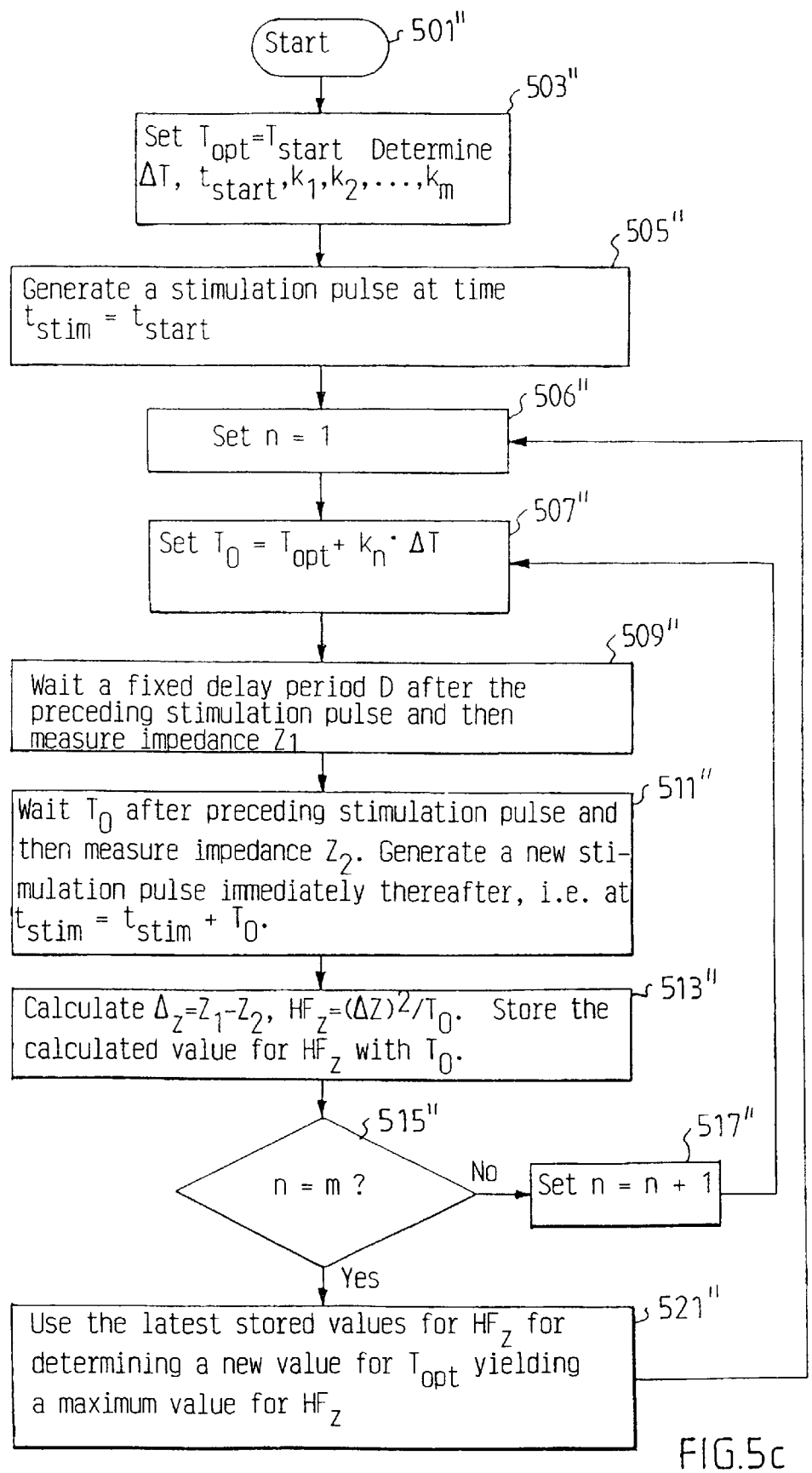

The procedural steps performed in an embodiment with more continuous adaptation of heart rate are shown in the flow chart in FIG. 5c. The procedure starts from a starting block 501", and parameter and starting values are then set in block 503". An optimal stimulation interval $T_{opt}$ is set at an appropriate starting value $T_{start}$. Moreover, time deviation $\Delta T$ is assigned an appropriate positive starting value. Moreover, an appropriate time $t_{start}$ is determined at which the first stimulation pulse is to be Generated. Moreover, values are determined for the coefficients $k_1, k_2 \ldots, k_m$ which are used with the fixed time deviation $\Delta T$ to form different time deviations. See below! Typical values can be m=4 and $k_1=1, k_2=-1, k_3=2, K_4=-2$ or $k_1=1, k_2-1, k_3=3, k_4 32-3$. A stimulation pulse is Generated in the next block 505 at time $t_{stim}=t_{start}$.

Figure 6:
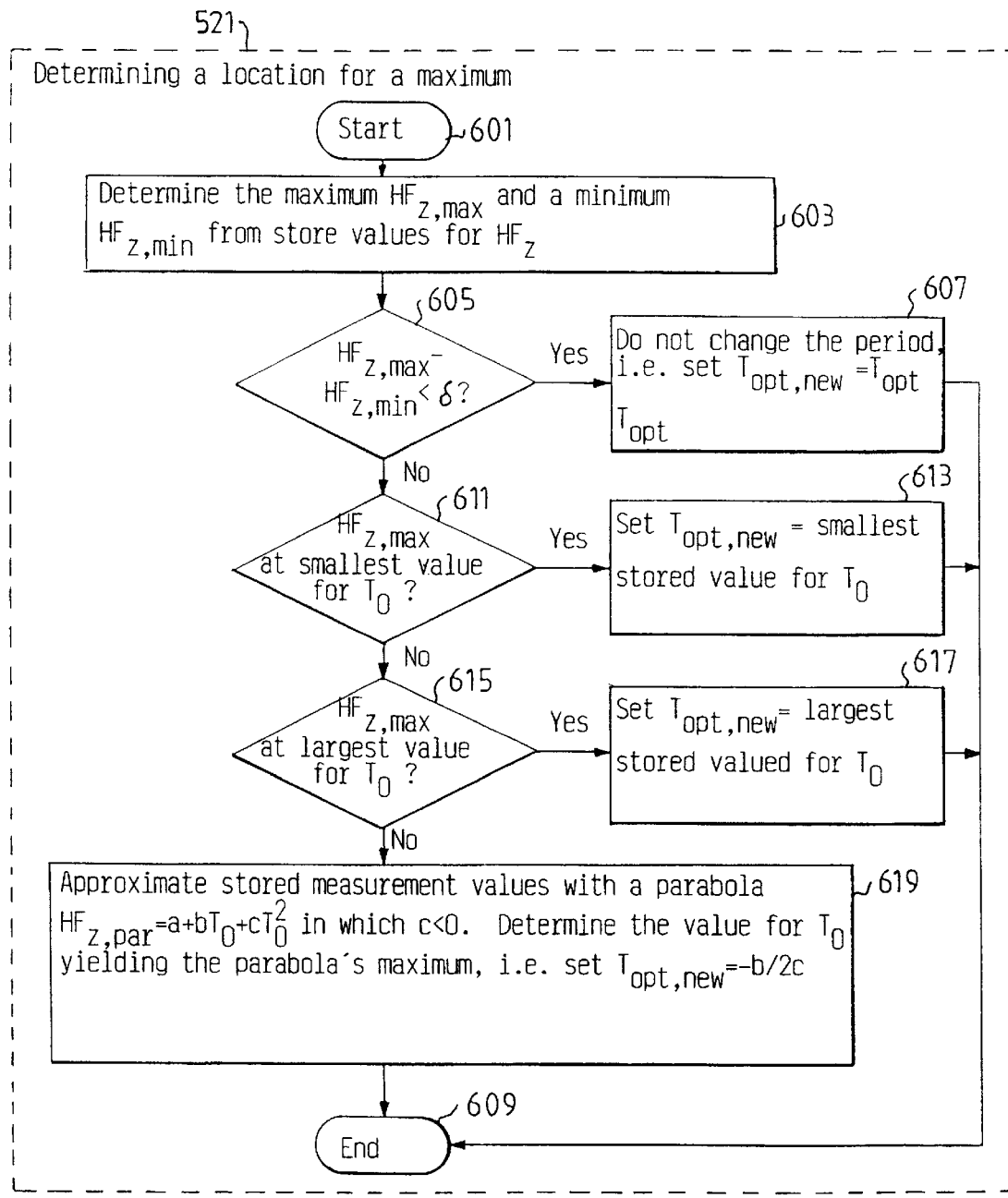
FIG. 6 is a flowchart for determining the rate value corresponding to a peak value of the auxiliary function calculated from measurement values in accordance with the invention.

A counter n in the next block 506" is assigned an initial value equal to one, and the heart cycle's next interval is then set at $T_0=T_{opt}+K_n\cdot\Delta T$ in block 507", i.e. it is assigned a duration which differs by $k_n\cdot\Delta T$ from the optimal duration $T_{opt}$ which is a reference value for the heart cycle and which is not directly used as a duration for an actual heart cycle. In the subsequent blocks 509"–513", the same tasks are performed as in blocks 509–513 in FIG. 5a. A query as to whether a sufficient number of new functional values are stored is then made in block 515". This is performed by comparing the counter value n with the fixed quantity m set. If this is not the case, the counter n is incremented one step in block 517", and block 507", which was described above, is executed to permit determination of additional functional values. If block 515" determines that the counter n has reached its final value, block 521" is performed. Block 521", like block 521' in FIG. 5b, compares stored functional values m to each other for determining the value $T_{opt}$ for the heart cycle duration yielding a maximum value for $HF_z$. Cf. FIG. 6. After this, a new determination of an optimal heart cycle duration is made, and the procedure switches to the above-described step 506" with initiation of the counter n, whereupon the determination loop 507"–519" is repeated m number of times.

It is obvious that the described procedures will only work with times between consecutive stimulation pulses, and no absolute times $t_{stim}, s_{start}$ need to be used. The time delays $\Delta T$ can be stated either as absolute values or expressed as a current stimulation duration $T_{opt}$. For example, the values $\Delta T=+2.5\%, -2.5\%+5\%, -5\%$ of $T_{opt}$ could be used in block 519' in FIG. 5b.

FIG. 6 shows a block diagram for a sub-routine which can be used for determining the value for heart cycle duration $T_0$ yielding a maximum value for $HF_z$. CF, blocks 521' and 521" in FIG. 5b and 5c respectively!. The routine starts in block 601, whereupon the maximum and minimum values for $HF_z$ in the four stored values are determined. They are designated $HF_{z,max}$ and $HF_{z,min}$. A determination is subsequently made in block 605 as to whether the variation in $HF_z$ values is small, i.e. is less than a selected small value $\delta$. If this is the case, the interval value used is acceptable, so $T_{opt,new}$ is set at $T_{opt}$ in block 607. After this, the routine concludes in end block 609. If block 605 determined that variation exceeds the value $\delta$, a block 611 determines whether the largest value for $HF_z$, i.e. $HF_{z,max}$, corresponds to the smallest value for $T_0$. If this is the case, the new interval $T_{opt,new}$ is set at this value in block 613. The routine then terminates again in block 609. If the determination in block 611 was negative, i.e. found that the largest value for $HF_z$ was not obtained at the smallest $T_0$, block 615 is performed instead. Here, a query is made, in the corresponding manner, as to whether the largest value for $HF_z$ is obtained at the highest $T_0$ value. If this is found to be the case, the new interval is set in a block at this value, i.e. $T_{opt,new}$. The routine again concludes in block 609.

If the query in block 615 resulted in a negative reply and a maximum was not obtained for either the largest or smallest $T_0$ value, a maximum must be obtained for a value between these $T_0$ values. A more demanding calculation is then made in block 619. First, stored measurement values are approximated, as noted above, with a second degree function or parabola $HF_{z,par}=a+bT_0+cT_0^2$ in which a, b, c are constants which must be numerically determined, and the constant c must also satisfy the condition c<0 so the parabola is a type with a maximum. The $T_0$ value is determined which yields this maximum, and the new interval, i.e. $T_{opt,new}$, is set equal to $-b/2c$. The routine is then concluded in block 609. After this, new determinations are made of functional values by varying cycle duration.

Thus, the method can revert e.g. to the flow chart in FIG. 5b in order to perform block 523'. Although modifications and changes may be suggested by those skilled in the art, it is the intention of the Inventors to embody within the patent warranted hereon all changes and modifications as reasonably and properly come within the scope of their contribution of the art.

What is claimed is:

1. An implantable heart stimulation device comprising:
   a pulse generator which generates a series of stimulation pulses at a variable rate;
   an electrode connected to said pulse generator and adapted for delivering said stimulation pulses in vivo to a heart;
   a control unit connected to said pulse generator for causing said pulse generator to emit the respective stimulation pulses at set times corresponding to respective at rates;
   a stroke volume at measuring unit for measuring respective stroke volumes of said heart at different rates of said stimulation pulses;
   a calculation unit, connected to said control unit and to said stroke volume measurement unit, for calculating values of an auxiliary function of two independent variables which, with the stroke volumes from said stroke volume measurement unit and the rates from said control unit as said two independent variables, produces a function of rate alone having an extreme point indicative of a calculated rate at which optimal heart functioning occurs; and
   an extreme point identifier, supplied with said values of said auxiliary function, which identifies said calculated rate, and that which is connected to said control unit and which supplies said calculated rate to said control unit, said control unit setting said times for emission of respective stimulation pulses dependent on said calculated rate.

2. An implantable heart stimulation device as claimed in claim 1, wherein said calculation unit employs an auxiliary function having said extreme point at a heart rate substantially at which a constant load and increasing heart rate change from increasing values to decreasing values.

3. A device as claimed in claim 1, wherein said calculation unit calculates said auxiliary function as a product of said heart rate raised to a selected expediential power and said stroke volume raised to a selected expediential power.

4. An implantable heart stimulation device as claimed in claim 3, wherein said selected expediential power of said heart rate comprises the second power, and wherein said second expediential power of said stroke volume comprises the second power.

5. An implantable heart stimulation device as claimed in claim 1, wherein said stroke volume measurement unit comprises a pair of electrodes adapted for a invivo implantation in a heart for measuring electrical impedance between said pair of electrodes.

6. An implantable heart stimulation device as claimed in claim 1, wherein said control unit changes an interval between successive stimulation pulses at selected time, differing from an interval between said times for emission of said respective stimulation pulses dependent on said calculating rate, and wherein said stroke volume measurement unit measures said stroke volume at said selected times.

7. An implantable heart stimulation device as claimed in claim 1, wherein said control unit constantly changes an interval between successive stimulation pulses from an interval corresponding to said times for emission of respective stimulation pulses dependent on said calculated rates, said control unit changing said interval with alternating signs and said stroke volume measurement unit determining said stroke volume for the changed intervals.

8. An implantable heart stimulation device as claimed in claim 1, wherein said control unit constantly changes an interval between successive stimulation pulses from said times for emission of respective stimulation pulses dependent on said calculated rate to different intervals, and wherein said stroke volume measures these stroke volume measures the stroke volume during said different intervals, said control unit maintaining an average interval between said stimulation pulses as being substantially equal to said interval for said times for emission of respective stimulation pulses dependent on said calculated rate.

9. A device for emitting stimulation pulses at a variable rate to a heart, comprising:
   a pulse generator which generates a series of stimulation pulses at a variable rate;
   an electrode connected to said pulse generator and adapted for delivering said stimulation pulses in vivo to a heart;
   impedance measuring means for measuring a change in the impedance in cardiac tissue during one heart cycle at times selected so that said change in impedance is indicative of a stroke volume of said heart during said one heart cycle;
   control means for changing an interval between successive stimulation pulses from an interval value corresponding to a reference value, said change in the impedance being obtained as a function of heart rate;
   calculation means connected to said impedance measuring means for determining stoke volume, and connected to said control means, said calculation means calculating an auxiliary function from two independent variables selected so that when the heart rate and the change in impedance as a function of heart rate are used as said variables instead of auxiliary function, a function of heart rate alone is obtained with an extreme point representing a heart rate value at which optimal cardiac function is achieved, said calculation means supplying said heart rate value to said control means for use as a new reference value.

10. A device as claimed in claim 9, wherein said calculation means comprises means for determining the heart rate HR using an auxiliary function $Hf_z = HR \cdot \Delta Z^2$, wherein $\Delta Z$ is said change in impedance, and said control unit supplying said heart rate HR to said control means for use as said new reference value.

* * * * *